(12) United States Patent
Bodkhe et al.

(10) Patent No.: US 10,457,613 B2
(45) Date of Patent: Oct. 29, 2019

(54) ANAEROBIC COLUMN REACTOR FOR BIODEGRADATION OF WASTES AND THE PROCESS THEREOF

(71) Applicant: Council of Scientific & Industrial Research, New Delhi (IN)

(72) Inventors: Sandeep Y. Bodkhe, Nagpur (IN); Atul N. Vaidya, Nagpur (IN)

(73) Assignee: Council of Scientific & Industrial Research, New Delhi (IN)

( * ) Notice: Subject to any disclaimer, the term of this patent is extended or adjusted under 35 U.S.C. 154(b) by 361 days.

(21) Appl. No.: 15/240,851

(22) Filed: Aug. 18, 2016

(65) Prior Publication Data

US 2017/0050892 A1 Feb. 23, 2017

(30) Foreign Application Priority Data

Aug. 19, 2015 (IN) ............................ 2549/DEL/2015

(51) Int. Cl.
*C05F 17/02* (2006.01)
*C02F 11/04* (2006.01)
(Continued)

(52) U.S. Cl.
CPC ........ *C05F 17/0247* (2013.01); *C02F 3/2866* (2013.01); *C02F 11/04* (2013.01); *C05F 9/02* (2013.01); *C05F 17/0018* (2013.01); *C05F 17/0027* (2013.01); *C05F 17/0036* (2013.01); *C05F 17/0258* (2013.01);
(Continued)

(58) Field of Classification Search
CPC .............. C05F 17/0247; C05F 17/0027; C05F 17/0258; C05F 17/0018; C05F 17/0036; C05F 9/02; C02F 11/04; C02F 3/2866; C02F 3/006; C02F 2103/26; C02F 2103/32; C02F 2103/20; C02F 2209/28; C02F 2209/06; C12M 23/02; C12M 21/04; C12M 27/00; Y02W 10/23; Y02W 30/43; Y02E 50/343; Y02P 20/145
USPC .......................................... 435/290.1–290.4
See application file for complete search history.

(56) References Cited

U.S. PATENT DOCUMENTS

| 4,532,042 A * | 7/1985 | Aivasidis ................. C02F 3/10 210/150 |
| 4,670,140 A | 6/1987 | Aivasidis et al. |

(Continued)

OTHER PUBLICATIONS

Kaul, S.N., Khanna, P. and Nandy, T. (1994); Biogas technologies—State-of-the-art; A document prepared ýby National Environmental Engineering Research Institute (NEERI) for Ministry of New and Renewable Energy Sources, Govt. of India pp. 130-140.

(Continued)

*Primary Examiner* — Michael L Hobbs
(74) *Attorney, Agent, or Firm* — Locke Lord LLP; Nicholas J. DiCeglie, Jr.

(57) ABSTRACT

The present invention relates to an anaerobic column reactor for biodegradation of wastes. Particularly the present invention relates to a process for conversion of biodegradable wastes to biogas and compost. More particularly, the present invention relates to an anaerobic reactor with unique arrangement of expanded and constricted portions alternatively placed vertically over each other which enhances the mixing pattern and thereby the mass transfer rates while controlling the biomass washout by regulating the upflow liquid velocity.

14 Claims, 1 Drawing Sheet

(51) Int. Cl.

| | | |
|---|---|---|
| *C12M 1/00* | (2006.01) | |
| *C02F 3/28* | (2006.01) | |
| *C12M 1/02* | (2006.01) | |
| *C12M 1/107* | (2006.01) | |
| *C05F 9/02* | (2006.01) | |
| *C05F 17/00* | (2006.01) | |
| *C02F 3/00* | (2006.01) | |
| *C02F 103/20* | (2006.01) | |
| *C02F 103/26* | (2006.01) | |
| *C02F 103/32* | (2006.01) | |

(52) U.S. Cl.
CPC .......... *C12M 21/04* (2013.01); *C12M 23/02* (2013.01); *C12M 23/34* (2013.01); *C12M 27/00* (2013.01); *C02F 3/006* (2013.01); *C02F 2103/20* (2013.01); *C02F 2103/26* (2013.01); *C02F 2103/32* (2013.01); *C02F 2209/06* (2013.01); *C02F 2209/38* (2013.01); *Y02E 50/343* (2013.01); *Y02P 20/145* (2015.11); *Y02W 10/23* (2015.05); *Y02W 30/43* (2015.05); *Y02W 30/47* (2015.05)

(56) References Cited

U.S. PATENT DOCUMENTS

| | | | |
|---|---|---|---|
| 5,670,047 | A | 9/1997 | Burke |
| 5,888,806 | A * | 3/1999 | Nguyen .................. C12P 7/10 435/289.1 |
| 6,482,643 | B2 * | 11/2002 | Yamane ............. C05F 17/0045 435/290.1 |
| 6,569,332 | B2 | 5/2003 | Ainsworth et al. |
| 7,311,834 | B2 | 12/2007 | Lee, Jr. |
| 7,320,753 | B2 | 1/2008 | Roos |
| 7,556,737 | B2 | 7/2009 | Zhang |
| 9,005,443 | B2 | 4/2015 | Arnoldsen, Jr. et al. |
| 2004/0025715 | A1 | 2/2004 | Bonde et al. |
| 2005/0130290 | A1 | 6/2005 | Choate et al. |

OTHER PUBLICATIONS

C. Ratanatamskul et al., "A prototype single-stage anaerobic digester for co-digestion of food waste and sewage sludge from high-rise building for on-site biogas production," International Biodeterioration & Biodegradation 95 (2014) 176-180.

Soli J. Arceiwala (1986); "Wastewater Treatment for Pollution Control and Reuse," Tata McGraw Hill Publishing Company Ltd, N. Delhi Book Chapter 3, Principles of Biological Treatment p. 42-59.

A. Bernstad et al., "Tank-connected food waste disposer systems—Current status and potential improvements," Waste Management 33 (2013) 193-203.

S.J. Grimberg et al., "Anaerobic digestion of food waste through the operation of a mesophilic two-phase pilot scale digester—Assessment of variable loadings on system performance," Bioresource Technology 178 (2015) 226-229.

Su Yun Xu et al., "Optimization of food waste hydrolysis in leach bed coupled with methanogenic reactor: Effect of pH and bulking agent," Bioresource Technology 102 (2011) 3702-3708.

Yiliang He et al., "High-concentration food wastewater treatment by an anaerobic membrane bioreactor," Water Research 39 (2005) 4110-4118.

Reeta Rani Singhania et al., "Recent advances in solid-state fermentation," Biochemical Engineering Journal 44 (2009) 13-18.

Jong Ik Park et al., "Long-term operation of slurry bioreactor for decomposition of food wastes," Bioresource Technology 84 (2002) 101-104.

T. Forster-Carneiro et al., "Influence of total solid and inoculum contents on performance of anaerobic reactors treating food waste," Bioresource Technology 99 (2008) 6994-7002.

Luis Ortega et al., "Thermophilic adaptation of a mesophilic anaerobic sludge for food waste treatment," Journal of Environmental Management 88 (2008) 517-525.

S. Di Berardino et al., "Semi-continuous anaerobic digestion of a food industry wastewater in an anaerobic filter," Bioresource Technology 71 (2000) 261-266.

L. Neves et al., "Influence of composition on the biomethanation potential of restaurant waste at mesophilic temperatures," Waste Management 28 (2008) 965-972.

Sandeep Yeshwant Bodkhey et al., "Concept and Application of Novel Anaerobic Reactor System for Decentralised Sewage Treatment," National Environmental Engineering Research Institute (NEERI), IND—Nagpur, Poster-Session Feb. 2, 2003.

A. Ahamed et al., "Multi-phased anaerobic baffled reactor treating food waste," Bioresource Technology 182 (2015) 239-244.

* cited by examiner

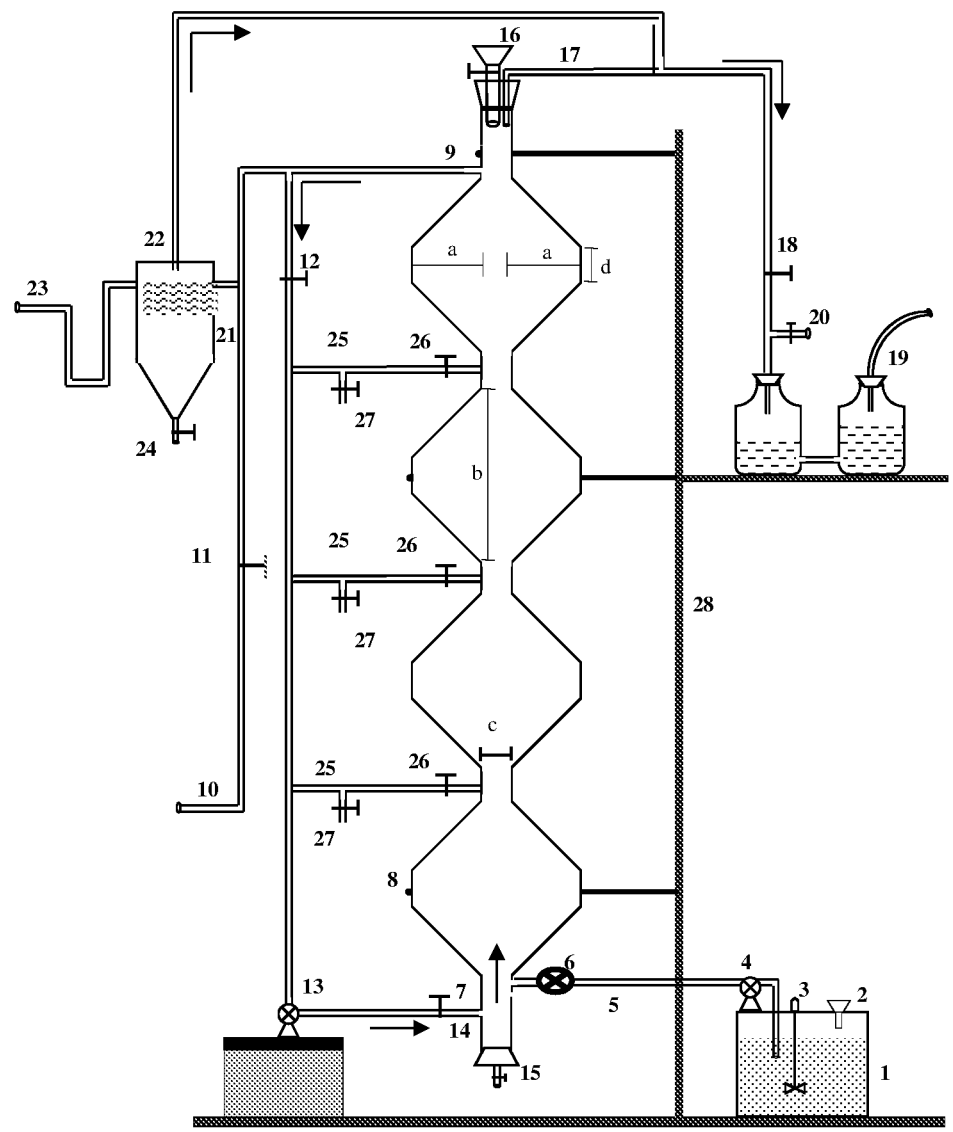

ANAEROBIC COLUMN REACTOR FOR BIODEGRADATION OF WASTES AND THE PROCESS THEREOF

CROSS REFERENCE TO RELATED APPLICATIONS

This application claims priority to Indian Patent Application No. 2549/DEL/2015, filed Aug. 19, 2015; the contents of which are hereby incorporated herein by reference.

FIELD OF THE INVENTION

The present invention relates to an anaerobic column reactor for biodegradation of wastes. Particularly the present invention relates to a process for conversion of biodegradable wastes to biogas and compost. More particularly, the present invention relates to an anaerobic reactor with unique arrangement of expanded and constricted portions alternatively placed vertically over each other which enhances the mixing pattern and thereby the mass transfer rates while controlling the biomass washout by regulating the upflow liquid velocity.

BACKGROUND AND PRIOR ART OF THE INVENTION

Aerobic treatment of solid wastes yields compost, but energy is not recovered and remains trapped in carbon content of the compost. In the process of biomethanation, the wastes are treated anaerobically to obtain energy in the form of methane gas. Biomethanation of solid wastes, particularly biodegradable wastes such as food wastes, agricultural residues and organic fractions of municipal solid wastes (MSW) is a promising technique for both, generating energy and reducing the volume of waste to be disposed of. Thus, it is realistic to consider such wastes as a renewable source for energy. Biomethanation does not require aeration and the sludge production is lower as compared to that in the aerobic processes. This further reduces the operational difficulties and costs associated with collection, transportation, storage and disposal of sludge. The solid state fermentation and anaerobic digestion are the most widely used methods for solid waste digestion.

Another reference may be made to Kaul, S. N., Khanna, P. and Nandy, T. (1994); Biogas technologies—State-of-the-art; A document prepared by National Environmental Engineering Research Institute (NEERI) for Ministry of New and Renewable Energy Sources, Govt. of India pp. 130-140; and Bodkhe, S. Y. (2003); Concept and application of a novel anaerobic reactor system for decentralized sewage treatment; Proceedings $5^{th}$ GVC—Wastewater Congress, Bremen (Germany), Vol. 2, pp. 557-563 wherein, all the existing anaerobic reactor systems conventionally adopted for wastewater treatment are categorized into two major categories:

Suspended growth system (SGS)
Attached growth system (AGS)

The drawbacks are: the reactors operated as suspended growth systems (SGS) such as most widely used upflow anaerobic sludge blanket (UASB) reactor; essentially needs granular sludge with good settling properties. At low hydraulic retention times (HRTs), increased upflow velocity of wastewater (i.e. higher hydraulic loading rate, HLR) causes biomass washout from the reactor. Reduced biomass availability for degrading increased organics at higher HLR ultimately deteriorates the performance efficiency of the reactor.

In attached growth system (AGS), e.g. anaerobic filter; porous inert packing media is provided to support the attachment of biomass. As the wastewater passes through the packed media, Suspended Solid (SS) present in the wastewater may develop progressive clogging of the packed bed and preferential hydraulic pathways may be created. This leads to short-circuiting of the movement of wastewater, which impairs the treatment efficiency of the reactor.

Reference may be made to Soli J. Arceiwala (1986); Wastewater Treatment for Pollution Control, Tata McGraw Hill Publications, N. Delhi, wherein much attention is sought towards the geometry of the UASB reactor and hydraulics for its proper functioning. A Gas-liquid-solid-separator (GLSS) is very much essential component of UASB for letting the gas to the gas collection channel at the top, while liquid rises through settler compartment and the solids settle back into the sludge zone. The upflow liquid velocity help form the sludge blanket. The drawback is that the development and maintenance of sludge blanket thickness and its retention at a particular height in reactor column for desirable period is extremely difficult and troublesome. This needs a great attention in reactor design, hydrodynamics and expertise in operation and maintenance.

Reference may be made to U.S. Pat. No. 5,670,047 by Burke; Dennis A., issued on 23 Sep. 1997, "Anaerobic treatment process for the rapid hydrolysis and conversion of organic materials to soluble and gaseous components", wherein it is stated that, two reactors are necessary for treatment of wastewater along with a mechanical or chemical separation technique to segregate particulate constituents from partially digested influent stream. The drawback is that, two reactors require more space, power, instrumentation, process control and maintenance. Besides this, particulate separation requires chemicals & mechanical installations, which consume overheads and electricity respectively, ultimately making the treatment uneconomical. This patented technology requires hydraulic retention time of 5 days. The technology including two reactors with mechanical accessories operating at high HRT may not be acceptable for industrial applications, as it may not prove cost-effective.

Another reference may be made to U.S. Pat. No. 6,569,332 by Anisworth, J. L., Alwood, D. and Rident, T. issued on 27 May 2003, "Integrated anaerobic digester system", wherein the digester employs pressurisable anaerobic digesters connected in parallel. The digester system is useful for biogas recovery from animal compost. The digesters needed mechanical agitation and biogas recirculation, along with digester sludge recirculation. The drawback is that, single digester vessel is not found adequate for digestion of comparatively easily biodegradable waste such as animal compost. The digester biogas is to be compressed upto 10 psi and recirculated through the digester besides digester sludge recirculation. The requirements such as compression and recirculation of biogas, recirculation of sludge and mechanical agitation within the digester need sophisticated mechanization and excessive power demand along with the expert operation and maintenance making the process less cost effective and easily adoptable.

Another reference may be made to U.S. Pat. No. 7,311,834 by Lee, Jr. and John, W. issued on 25 Dec. 2007, "Apparatus for the treatment of particulate biodegradable organic waste", wherein the apparatus consist of thermal hydrolysis reactor operating at 130° C. and pressure at saturated water vapor pressure to produce solubilized organic material at pH above 3.15, and a separation mechanism to separate solubilized organic material and residual solids in an anaerobic reactor for digestion of solubilized organic material. The drawback is that operation and maintenance of two-phase anaerobic digestion system at higher temperature and pressure with separation mechanism need more space, spares and energy along with sophisticated mechanization ultimately rendering the treatment system less user friendly and less energy efficient. The compactness of the system is lost due to its requirement of separation mechanism.

Another reference may be made to U.S. Pat. No. 7,556,737 by Zhang, R., issued on 7 Jul. 2009, "Anaerobic phased solids (APS) digester for biogas production from organic solid wastes", wherein a two phase anaerobic system (APS) is proposed for digestion of organic substrates to generate methane. The APS consists of a hydrolysis reactor, a buffer tank and a biogasification reactor. The drawback is that, the two-phase system has two sets of bioreactors along with a buffer tank. The operation, maintenance, space and energy consumption of two phase reactor system is higher if not double than that of the single phase reactor system.

Another reference may be made to Ortega, L., Barrington, S., Fuirt, S. R. (2008), Thermophilic adaptation of a mesophilic anaerobic sludge for food waste treatment. Journal of Environmental Management, 88, pp. 517-525, wherein UASB reactor (5 L) was operated in batch mode under the thermophilic condition (55° C.) at 10 d HRT. The drawback is that, the UASB face a serious problem of biomass washout at lower HRT and at higher OLR. The thermophilic operation is not economically attractive. The batch operation of UASB might not sustain the sludge blanket and hence the continuous operation is recommended by the authors, defeating the sole concept of UASB reactor.

Another reference may be made to Forster Carneiro, T., Perez, M., and Romero, L. I. (2008), "Influence of total solid inoculum contents on performance of anaerobic reactors treating food wastes; Bioresource Technology, 99, pp. 6994-7002, wherein, the biomethanation process of food waste was analyzed in a batch reactor with three different percentages of solids and inoculum. The best performance was observed with 20% of total solids and 30% of inoculum, which gave methane yield of 0.22 g $CH_4$/gVS. The drawback is that, the reactor being a batch type, it cannot be used for the places where the food waste is continuously generated. The batch reactors are generally less efficient than continuous reactors.

Another reference may be made to Neves, L., Goncalo, E., Oliveira, R. and Alves, M. M. (2008), Influence of composition on the biomethanation potential of restaurant waste at mesophilic temperatures, Waste Management, 28, pp. 965-972, wherein batch degradation of restaurant waste under methanogenic conditions was carried out. The drawback is that the process has the longer time requirement of 30 days to attain not more than 85% biodegradability. The study was conducted under specific experimental/control conditions which are difficult to maintain in the field and hence the results obtained may not be warranted.

Another reference may be made to Berandino, S. D., Corta, S. and Converti, A., (2000), Semi-continuous anaerobic digestion of a food industry wastewater in an anaerobic filter, Bioresource Technology, 71, pp. 261-266, wherein, a 10 L anaerobic filter was operated at 35° C. semi-continuously with total solid concentration of 2-3 g/L and COD of 2.52 g/L at HRT of 5 d. The COD removal efficiency obtained was above 80%. The drawback is that the anaerobic filter under longer operating period and/or with higher concentration of total solids the process/system cannot be useful. Moreover, the system cannot be useful for the treatment of slurries, the form in which food waste is generally disposed of. Under high solid concentration and longer period of operation, the anaerobic filter gets clogged and the overall efficiency of the reactor deteriorates. The backwash required to remove clogging needs water and energy besides additional mechanization.

Another reference may be made to He, Y., Xu, P., Li, C., and Zhang, B. (2005), High concentration food wastewater treatment by an anaerobic membrane bioreactor, Water Research, 39, pp. 4110-4118, wherein, ultrafiltration membrane bioreactor was used for treatment of high strength food wastewater. The drawback is that significant flux decline is caused by the formation of a thick biofouling layer. The membrane bioreactor needs expertise to operate, chemicals for washings and the process is not energy efficient and hence cannot be useful for the treatment of huge amount of food waste slurries.

Another reference may be made to R. R. Singhania, A. K. Patel, C. R. Soccol, A. Pandey (2009), Recent advances in solid-state fermentation, Biochemical Engineering Journal, 44(1), pp. 13-18 wherein the solid state fermentation of biodegradable wastes has been found to be economically feasible. The drawbacks are: it faces the challenges such as difficulties on scale-up, poor mixing and hence the low mass transfer rates, weak control of process parameters (pH, heat, moisture, nutrient conditions, etc.), problems with heat build-up, higher impurity product, increasing recovery product costs Another reference may be made to Jong Ik Park, Yeoung-Sang Yun, Jong Moon Park (2002), Long-term operation of slurry bioreactor for decomposition of food wastes, Bioresource Technology, 84, pp. 101-104 wherein aerobic digestion of food waste was carried out in an 80 L stirred tank reactor (50 L working volume) used as a slurry bioreactor. The reactor was equipped with a pitched blade turbine-type impeller and sparger for agitation and aeration, respectively. The reactor was operated with a waste addition rate of 3 g dw/L/day, an agitation speed of 120 rpm and aeration rate of 50 L/min. Using data for time variation of dissolved oxygen, the oxygen requirement for decomposition of food wastes was estimated to be 5.0 g $O_2$ $g^{-1}$ dry weight of food wastes. During operation for 90 days, 91% reduction of food wastes was achieved. The drawback is that the aerobic slurry bioreactor consumes dissolved oxygen along with a mechanism to supply and mix oxygen with food slurry and energy to carry out these operations. Thus, the aerobic treatment of food waste is energy intensive, need mechanical installations and expert O&M.

Another reference may be drawn to US Patent No. US2004/002571A1 by Bone, T., Pedersen, L. J., issued on 12 Feb. 2004, "Concept for slurry separation and biogas production", wherein anaerobic digestion of animal composts, energy crops and other similar organic substrates has been considered for biogas generation. The drawback is that, the patent discusses only the concept of biomass slurry preparation and does not specify any reactor technology to be exploited for biogas production.

Another reference may be drawn to Xu, S. Y., Lam, H. P., Karthikeyan, O. P., Wong, J. W. C. (2011), optimization of food waste hydrolysis in leach bed coupled with methanogenic reactor: effect of pH and bulking agent, Bioresource Technology, 102(4) pp. 3702-3708, wherein, leach bed reactor (LBR) was coupled with methanogenic UASB reactor, for the treatment of food waste. The drawback is that it needed operation and maintenance of two reactors with additional requirement of leachate recirculation. The LBR needed bulking agents or co-substrates for methanation. The strong control over acidogenesis was essentially recommended. The use of bulking agents affected the working volume of the reactor. The reduced reactor volume increases the cost of the treatment.

Another reference may be drawn to Bernstad, A., Davidsson, A., Tasi, J., Persson, E. Bissmant, M. Jansen, J. Lacour (2013), Tank connected food waste disposer systems—current status and potential improvements, Waste Management, 33, pp. 193-203, wherein, unconventional system for separate collection of ground food waste and its settling was carried out for methane generation. The drawback is that, the system is operated on the principles of two-phase anaerobic process inheriting their drawbacks as pointed out earlier. The system comprised of disposer and settling tanks. The fugitive emissions of methane from the settling tanks were also observed. Such fugitive emissions reduce the inventory of the biogas and cause, on the contrary, the greenhouse effect.

Another reference may be drawn to Ratanatamskul, C., Onnum, G., Yamamoto K. (2014), A prototype single-stage anaerobic digester for co-digestion of food waste and sewage sludge from high-rise building for on-site biogas production, International Biodeterioration & Biodegradation, 95, Part A, pp. 176-180, wherein, co-digestion of food waste (FW) and sewage sludge (SWS) was carried out with the help of a prototype single-stage anaerobic digester. The prototype system was efficiently producing methane at hydraulic retention time (HRT) of 27 days corresponding to organic loading rates of 7.9 kgCOD/m3.d. The feed mixed waste ratio (FW/SWS) of 10:1 by weight was selected. The drawback is that, the system uses a co-digestion technique thereby curtailing the capacity of the system to treat food waste. The system is operated at the long HRT of 27 days for satisfactory generation of methane. Reactor operation at long HRT reduces cost-effectiveness of the treatment system.

Another reference may be made to U.S. Pat. No. 9,005,443, 14 Apr. 2015 by Arnoldsen, Jr.; Ronald E. Arnoldsen; Debra A. "Compartmentalized anaerobic digesters" wherein an anaerobic digestion device includes a digester body configured to receive organic waste and a plurality of plates coupled to one another so as to divide an interior volume of the digester body into a plurality of compartmentalized chambers. The compartmentalized chambers are movable relative to the digester body to advance slurry of said organic waste along a length of the digester body. A plurality of ports spaced along the digester body and arranged to vent biogas from the digester body. A storage vessel is configured to receive and store biogas received from the digester body via the ports, and a heating system configured to heat the digester body. The heating system is fuelled by the biogas vented from the digester body. The drawback is that the overall configuration of the system is extremely complicated in construction and operation and maintenance. The system needs a heating system to operate it at optimum conditions. In some exemplary aspects, a need of water containing an anti-freezing solvent may be heated by the water heater and then circulated through one or more flow lines. An insulator may be placed about the hot water tubing and digester body for efficiency. Hence, it may not be a cost-effective way of treatment of wastes.

Another reference may be made to S. J. Grimberg, D. Hilderbrandt, M. Kinnunen, S. Rogers (2015), "Anaerobic digestion of food waste through the operation of a mesophilic two-phase pilot scale digester—Assessment of variable loadings on system performance" Bioresource Technology, Volume 178, Pages 226-229 wherein, Single and two-phase operations were compared at mesophilic operating conditions using a digester system consisting of three 5-m$^3$ reactors treating food waste generated daily within the university campus kitchens. When normalizing the methane production to the daily feedstock characteristics, significantly greater methane was produced during two-phase mesophilic digestion compared to the single-stage operation (methane yield of 380 vs 446-L $CH_4$ kg $VS^{-1}$; 359 vs 481-L $CH_4$ kg $COD^{-1}$ removed for single vs two stage operation). The fermentation reactor could be maintained reliably even under very low loading rates (0.79±0.16 kg COD $m^{-3}$ $d^{-1}$) maintaining a steady state pH of 5.2. The drawback is that despite the potential difficulties with operating the more complex system, the two-stage process could be successfully maintained through low-loading periods as are typically experienced during summer months on a university campus. Therefore, it is usual that the system has experienced many overloading upsets. No significant difference was observed in the effluent concentrations of single-stage vs two-stage operation. There was no significant difference in the average total methane produced per day between the single-stage and two-stage system. The pH of fermentation reactor goes down up to 5.2, whereas the pH at methanogenic reactor has to be maintained at above 7.0 for its optimum operation by addition of alkali. This increases the cost of operation and maintenance.

Another reference may be made to U.S. Pat. No. 7,320,753, Jan. 22, 2008 by Kurt Frederich Roos, "Anaerobic digester system for animal waste stabilization and biogas recovery", wherein, an anaerobic digester system comprising a substantially flexible bladder for anaerobically digesting animal waste, with biogas production and recovery is given. The substantially flexible bladder has one or more waste inlets, digester effluent outlets, sludge access ports, and biogas outlets on a top surface thereof. The bladder and the one or more biogas storage containers may be constructed with reinforced geo-membrane material. The bladder may include an internal baffle defining a U-shaped interior having an inlet side and an outlet side. The bladder, for primary waste treatment, may be complemented by other structures for secondary and tertiary waste treatments. As biogas is produced inside the bladder, the waste is pushed out of the digester effluent outlet into the external displacement tank and when biogas is used, the displaced waste flows back into the bladder through the digester effluent outlet. The drawback is that the construction of the digestor and biogas collection system is very complicated and the operation demands expertise. The material of construction of substantially flexible bladder is essentially reinforced geo-membrane. The cost of construction is high and only specific material is to be used for construction. The bladder, for primary waste treatment, may be complemented by other structures for secondary and tertiary waste treatments.

Another reference may be made to US Patent No. 0130290A1 Jun. 16, 2005 by Choate, Chris E.; Sherman, Paul A. "Organic waste material treatment system", wherein, a system for treating organic waste material, via a multi-stage process involving anaerobic hydrolysis, anaerobic digestion of the liquid hydrolysis product, and aerobic composting of the solids remaining after hydrolysis is given. The organic waste materials may be pre-treated by adding a amount of liquid inoculant sufficient to raise the moisture content of the organic waste to a minimum of 60%. The organic waste material is then placed within a sealed hydrolysis vessel, which may take the form of a cylindrical polymer bag. The liquid hydrolysis product transferred from the vessel, which may be temporarily stored in a holding tank, is passed to a conventional anaerobic digester. In a thermophilic digester, methanogenic bacteria convert organic matter that is dissolved and/or suspended in the liquid hydrolysis product to a biogas product. The drawback is that a multi-stage process is involved in the process of digestion, which include, pre-treatment of waste, anaerobic hydrolysis, anaerobic digestion of the liquid hydrolysis product, and aerobic composting of the solids remaining after hydrolysis. The basic reactor used is a conventional thermophillic anaerobic digester. This means that there would be no benefit on the rate of biogas production. Rather, the treatment sceme is very lengthy and requires many reactors.

Another reference may be made to A. Ahamed, C. L. Chen, R. Rajagopal, D. Wu, Y. Mao, I. J. R. Ho, J. W. Lim, J.-Y. Wang (2015), Multi-phased anaerobic baffled reactor treating food waste, Bioresource Technology, Volume 182, Pages 239-244, wherein, the study was conducted to identify the performance of a multi-phased anaerobic baffled reactor (MP-ABR) with food waste (FW) as the substrate for biogas production and thereby to promote an efficient energy recovery and treatment method for the wastes with high organic solid content through phase separation. A four-chambered ABR was operated at an HRT of 30 days with an OLR of 0.5-1.0 g-VS/L d for a period of 175 days at 35±1° C. Consistent overall removal efficiencies of 85.3% (COD), 94.5% ($COD_s$), 89.6% (VFA) and 86.4% (VS) were observed throughout the experiment displaying a great potential to treat FW. Biogas generated was 215.57 mL/g-$VS_{removed}$ d. Phase separation was observed and supported by the COD and VFA trends, and an efficient recovery of bioenergy from FW was achieved. The drawback is that considering the total reactor volume of MP-ABR in this study, the biogas production is relatively low which is 88.45 mL/L of the reactor volume. The reactor was operated in two operational periods with a modification to the reactor configuration in the second period. This is not feasible in actual practise. To prove the feasibility, pilot scale systems should be operated. Each compartment was provided with an overhead mixer rotating at a speed of 100-150 rpm to minimize dead zones and short circuiting. Basically, ABR is not meant for treatment of food waste. The dead zones and short circuiting impair the performance. Overhead mixers create chances of biogas leakages.

The publications and patents cited above on anaerobic treatment/biomethanation of organic wastes/substrates indicated the process of slurry preparation/feed to the anaerobic digestion in general and the operation of anaerobic reactor/anaerobic digestion apparatus in particular. The apparatus/devices used for biomethanation of wastes are conventional reactors; used as a methanation phase/reactor in a two phase biomethanation/digestion system.

The operation and maintenance (O&M) of the two-phase digestion (acidogenesis and methanaogenesis) systems consumes space, energy, chemicals to yield the efficient biomethanation potential. Moreover, the conventional reactors used for methanogenesis part carry inherent demerits. These aspects together render the existing systems techno-economically unviable for biomethanation of biodegradable wastes/slurries. Hence, the present invention proposes a single reactor for biomethanation of wastes at mesophilic temperatures.

OBJECTIVES OF THE INVENTION

The main object of the present invention is to provide an anaerobic column reactor for biodegradation of wastes.

Another object of the present invention is to provide a process for conversion of biodegradable matter to biogas and compost.

Yet another object of the present invention is to provide the anaerobic reactor with unique arrangement of expanded and constricted portions alternatively placed vertically over each other which enhances the mixing pattern and thereby the mass transfer rates while controlling the biomass washout by regulating the upflow liquid velocity.

SUMMARY OF THE INVENTION

Accordingly, the present invention provides a anaerobic column reactor for conversion of biodegradable organic matter present in wastewaters and solid wastes into biogas and compost; said reactor consisting essentially of a column of at least four expanded portions (EP), connected to each other by constricted portions (CP), waste feeding and chemicals feeding facility, biogas collection sampling and measurement assembly, slurry/digestate recirculation assembly, with backwash facility.

In an embodiment of the present invention, an anaerobic column reactor (100) for biodegradation of wastes comprising of a feed tank (1) equipped with waste feeding funnel (2), mixing arrangement (3), feed pump (4), inlet pipe (5), regulating valves (6), said reactor (100) is having a constricted portion (7) and expanded portion (8), recirculation pipe (9), outlet (10), valves (11) and (12), slurry recirculation facility (13) (14) (15), chemicals feeding facility (16), biogas collection facility (17) and (18) sampling and measurement assembly (19) (20) connected to settling tank (21), biogas collection assembly (22) connected with outlet (23), sludge disposal outlet (24), and slurry/digestate recirculation arrangement (25) connected with valves (26) (27) and a stand to support the reactor assembly (28).

In another embodiment of the present invention, the reactor (100) consisting a column of at least four alternate (please define this term) expanded portions (8) connected to each other by constricted portions (7).

In another embodiment of the present invention, alternate expanded portions (8) and constricted portions (7) are connected in series that the reactor has a single outlet (23) and single biogas collection point.

In yet another embodiment of the present invention, the reactor (100) is operated in a batch mode, semi-continuous or continuous mode with automated or manual operation possible.

In a preferred embodiment of the present invention, alternate expanded portions (8) are interconnected through a recirculation pipe (9) is facilitate recirculation of digested from a particular expanded portion (8) with the help of the inlet (5) connected with controlling valves (6).

In still another embodiment of the present invention, biogas collection assembly (17, 18, 22), sampling and measurement assembly (19, 20) is provided to facilitate biogas collection from the reactor (100) and settling tank (21).

In another embodiment of the present invention, the funnel (2, 16) with valve (6) is being used for waste feeding and chemicals feeding facility respectively.

In yet another embodiment of the present invention, settling tank (21) is provided with effluent outlet (23) for removal of clarified effluent and sludge disposal outlet (24) at the bottom of the settling tank (21) for the discharge of the settled sludge.

In still another embodiment of the present invention, mixed culture consortia of anaerobic microorganisms is being used to digest organic biodegradable waste to biogas and compost.

In a preferred embodiment of the present invention, the biodegradable wastes is selected from biodegradable solid wastes, waste water and aqueous slurry of biomass, fruits, vegetables, agro-processing waste, animal compost, poultry wastes, aquatic plants, fraction of municipal solid wastes, energy crops and combinations thereof.

In yet another embodiment of the present invention, a process for the conversion of biodegradable wastes into biogas and compost by using the reactor as claimed in claim 1, wherein the process steps comprises:
  a. pumping the wastes and passing from inlet (5) at the bottom to outlet (23) at the top through constricted portion (7) and expanded portion (8);
  b. degrading wastes by mixing wastes with the culture of consortia anaerobic microorganisms in in the reactor to obtain slurry;
  c. recirculating the slurry obtained in step (b) in the reactor through recirculation pump (9) to produce biogas;
  d. collecting the biogas generated in step (c) from settling tank (21) and biogas collection assembly (17, 18) sampling and measurement assembly (19, 20);
  e. collecting sludge from the setting tank (21) through sludge disposal outlet obtained in step (c) and sent for its disposal.

In yet another embodiment of the present invention, the waste flows into the next EP through constricted portion (CP).

In yet another embodiment of the present invention, the anaerobic column reactor for conversion of biodegradable organic matter present in wastewaters and solid wastes into methane energy and compost;

In yet another embodiment of the present invention, the expanded portions individual comprises tapped side walls, the lower side walls assist in retaining of the biosolids by settling and the upper tapered side wall prevents escape of solids along with biogas bubbles and effluent out of the reactor.

In yet another embodiment of the present invention, the biogas bubbles create the turbulence and provide a gentle mixing of sludge and organic matter, which enhances biomass substrate contact, and thereby improves substrate removal rate through improved mass transfer. The mixing imparted by biogas avoids mechanical mixing requirement ultimately saving the costs associated with mixing devices, power and operation & maintenance.

In yet another embodiment of the present invention, outlet of the reactor is provided in the form of inverted siphon with water seal at outlet to restrict the biogas produced in reactor from escaping along with the treated effluent.

In yet another embodiment of the present invention, the constricted portion of column reactor is provided to increase the velocity of the feed flow entering into expanded portion and to enroute the flow through the sludge bed. The evenly distributed feed flow directed towards centre maximizes mixing of biomass with substrate and thereby enhances the mass transfer rate.

In still another embodiment of the present invention, sampling ports are provided to all the expanded portions of the reactor to collect the samples from individual expanded portions so as to calculate treatment efficiency by the particular EP.

In still another embodiment of the present invention, free space provided at the top of reactor forms the biogas collection zone and utilized for accumulation of the biogas produced during the anaerobic biodegradation of organic matter then tapped from the gas collection manifold, provided at the top of the reactor.

BRIEF DESCRIPTION OF THE DRAWING

The Figure: represents the sectional view of the reactor system embodying the present invention. It shows the arrangement for biogas collection and digestate disposal.

The numerals indicate the respective parts of the reactor system shown in the same sheet and are described as follows:
  1. Represents Feed tank
  2. Represents Funnel to add solid/liquid material to feed tank
  3. Represents Mixer/Impeller/blender
  4. Represents Pumping mechanism for inlet flow
  5. Represents Inlet to reactor
  6. Represents non return valve to control inlet flow
  7. Represents Constricted portion
  8. Represents Expanded portion
  9. Represents recirculation pipe
  10. Represents Outlet of reactor
  11. Represents valve to control the effluent discharge
  12. Represents valve to control the recirculation rate
  13. Represents slurry/digestate recirculation pump
  14. Represents slurry/digestate recirculation in the reactor
  15. Represents slurry/digestate withdraw backwash facility
  16. Represents feed funnel for direct feeding of waste/chemicals
  17. Represents biogas collection
  18. Represents valve to control the biogas flow
  19. Represents biogas collection measurement flaring arrangement
  20. Represents biogas sampling port
  21. Represents settling tank
  22. Represents biogas collection from settling tank
  23. Represents outlet of settling tank
  24. Represents outlet for sludge disposal
  25. Represents slurry/digestate sampling cum recirculation arrangement from individual CP
  26. Represents value to control/regulate recirculation
  27. Represents value to sampling port
  28. Represents to support the reactor

DETAILED DESCRIPTION OF THE INVENTION

The anaerobic column reactor system has various parts as described in the drawings (FIG. 1 represents the sectional elevation of the reactor indicating provision and locations of all the EP and CP along with valves, piping and instruments involved) and described earlier. The invention consists of anaerobic column reactor and other accessories forming a treatment system. The feed tank is provided which can hold the liquefied solid waste/waste slurry and/or to provide mixing. The addition of chemical solutions is possible in the same mixing/feed tank. The impeller type of mixing arrangement is provided in the tank to maintain the consistency of the waste slurry. The slurry can be fed to the reactor by a slurry pump mounted on the feed tank through the inlet. The identical flow pattern is followed in all the constricted and expanded portions.

The reactor design is such that the turbulence and eddies formed within the reactor help accelerate the mixing of waste with the biomass, thereby enhancing the organism-organics, contact ultimately accelerating the mass transfer rate and eliminating mixing devices. Additional mechanisms for mixing, equalization are not needed as they occur simultaneously with the anaerobic digestion thus saving time, cost of treatment, and operation and maintenance. The invention eliminates problems related to biomass washout at lower hydraulic retention times (HRT), which is a usual problem in all the continuously operated, suspended growth type of anaerobic reactors. The reactor does not require granular and flocculated sludge as necessary in upflow anaerobic sludge blanket reactor (UASB). The invention is made suitable for treatment of but not restricted to low, medium and even high strength biodegradable wastes (solid/liquid) sludge digestion and slurry biodegradation. The reactor is equally useful for the anaerobic treatment of liquid and solid wastes individually and in combination. The configuration and hydraulics of the reactor significantly reduces the floor area requirement and pumping energy requirement considerably as compared to the existing treatment systems.

The present invention is to provide an anaerobic column reactor for biomethanation of wastes and the process thereof, which obviates the drawbacks of the hitherto known prior art as detailed above. Further the present invention is to provide an anaerobic reactor system, which facilitates effective biomethanation of but not restricted to solid/liquid biodegradable wastes and its slurry for efficient biogas recovery as compared to conventional reactor systems known in the prior art. The present invention is to provide anaerobic column reactor system with a definite hydraulics by virtue of which it does not need granular and flocculent biomass, which otherwise is a prerequisite for suspended growth anaerobic reactors. This reduces start-up periods and provides flexibility in operating the reactor.

In the present invention anaerobic column reactor does not require a porous packing media matrix as required in conventional anaerobic fixed film reactors for biofilm growth. This feature of the configuration not only saves the cost of media, reducing the capital cost of the treatment systems, but precludes it from reducing reactor's effective working volume also. Besides, problems such as clogging of media followed by channeling and short-circuiting, which subsequently impairs the treatment efficiency, are also eliminated. The reactor system used in series or in parallel mode, which will have single gas collection port without gas/solid or solid/liquid separation facility requirements.

The anaerobic column reactor configuration, with definite hydrodynamics by virtue of which the need for mechanical and/or any other mode of mixing is eliminated. The anaerobic column reactor provides high sludge retention time (SRT) at relatively small reactor volume/low HRT, effecting higher treatment efficiency. In the anaerobic column reactor, wherein the improved configuration allows partial phase segregation of different phases of anaerobic digestion such as hydrolysis, acidogenesis and methanogenesis etc. within the same reactor. This facet eliminates need for separate reactors for carrying out different phase reactions.

In the anaerobic column reactor wastewaters and solid waste are converted to produce useful resources such as biogas and compost. The anaerobic column reactor minimizes environmental pollution by converting organic fraction of the waste to resources such as fertilizer and methane. The most essential requirements of other anaerobic reactors are met with by virtue of the configuration such as mixing of organics with organisms; partial phase segregation of acidogenic and methanogenic phases within same reactor; solid-liquid-gas separation without any special provision of separator; single pump required for pumping, mixing, recirculating etc.

The innovative reactor configuration creates controlled turbulence which facilitates enhanced mixing while preventing biomass washout, thus eliminating mechanisms/devices for reactor mixing and biomass control. The reactor geometry facilitates the partial phase separation of different phases of anaerobic biodegradation along the height of the column allowing the individual processes to occur at their maximum reaction rates. Therefore, use of this reactor circumvents use of multiple reactors for different phases thereby saving in associated construction and O&M costs.

The anaerobic reactors present in the market are suitable for treatment of either wastewater or slurry of solid waste. This invention suits well to both, liquid and the solid wastes as well and facilitates energy generation and waste byproduct recovery. This invention is very promising for efficient and cost-effective application of biomethanation of solid wastes, particularly biodegradable wastes such as food wastes, agricultural residues and organic fractions of municipal solid wastes generating energy and reducing the volume of waste to be disposed of. The reactor is also useful for biomethanation of all the wastewaters containing organic matter such as municipal wastewater, and industrial wastewaters from distillery, dairy, food, tannery, sugar, and sewage.

This patent discloses an anaerobic column reactor and its operational procedure for anaerobic digestion of organic materials such as sewage sludge, municipal waste, animal waste and all other wastes containing biodegradable organic matter. While eliminating drawbacks of existing treatment systems, present invention carries several meritorious.

The present invention concerns to an anaerobic column reactor for efficient recovery of biogas and compost from organic substrates present in wastewaters and solid wastes. This reactor is successful in promoting efficient and consistent performance by virtue of its capability to maintain sufficient quantum of viable biomass and rigorous mixing conditions enabling maximum mass transfer rates without additional devices necessary for mixing and biosolids retention. The reactor hydrodynamics induces controlled turbulence which enhances the mixing while preventing biomass washout. The reactor is compact, modular design easy for retrofication and transport for the in-situ applications. It can be operated in all the modes such as batch, semi-continuous and continuous mode.

The reactor having interconnected constricted and expanded portions in series form one unit. N number of such units can be put in series or in parallel as per the desired degree of treatment. The shape of the constricted portion (CP) and the expanded portion (EP) can be of but not restricted to spherical shape. The constricted portion should preferably be but not restricted to tubular shape. It can be of any length with a requirement of accommodating the external connection such as sampling ports or recirculating assembly. The height of the expanded portion and outermost port of expanded portion are 'b' and 'd' respectively. The dimension 'a' represents the distance between wall of constricted portion and outermost portion. The diameter of constricted portion is 'c'. the dimensions are designed but not restricted in such a way that b=2a+c. Preferably the column reactor should be designed in such a way that the dimension should be b>2a; c≤d. The ratio of (2a+d)/d should preferably be but not restricted to the range from 0.33 to 0.50. Larger diameter of the constricted portion would not be able to create sufficient upflow liquid velocity through the constricted portion needed for keeping the substrate, particularly particulate matter, in suspension. Whereas, the narrower diameter of the constricted portion than the specified range can cause the disintegration of the sludge granules and can also washout the biomass out of the reactor. Depending upon the quality of organic waste in general and the particle size and density of the slurry in particular, the specific ratio selection is made.

The upper tapered section of the EP acts like a gas-solid-liquid separator. The liquid upflow velocity imparted by the constricted portion (CP) imparts the buoyancy to the biomass. The combined effect of solid setting and buoyancy creates rigorous mixing conditions in the middle of the EP. The improved mixing conditions accelerate the mass transfer rates and further the rate of degradation.

The digested or the reactor content can also be recirculated to the desired portion of the reactor. The positioning of the valves is made in such a way that recirculation of the biomass from particular portion of the reactor to the desired portion can be done with the help of a pump.

Finally, the treated effluent is collected from the outlet. The biogas generated is collected through gas manifolds and stored for its appropriate use. Except feed pump and recirculation pump there are no other mechanical moving parts in the system. Hence it becomes very sturdy, compact, reliable, easy to operate, zero maintenance reactor system.

The outlet is provided in the form of inverted syphon, so that the biogas escaping with the effluent is arrested. The gas manifold is provided at the top of the reactor to collect the biogas and route it to collection and measurement assembly.

The treated effluent slurry/digestate is collected in the settling tank. The hopper bottom of the settling tank facilitates the collection of the sludge and its subsequent disposal by suitable means as per standard procedure. The liquid part of the settling tank is collected and used for further slurry preparation. Such a procedure helps in curtailing the fresh water requirements for slurry preparation. The biogas from the tank is collected and sent to the measurement assembly. The funnel with valve at the top is provided to feed the reactor with alkali and/or nutrients. The valve provided at the bottom of reactor helps to discharge the reactor content whenever needed. It can also be used for backwashing of the reactor as and when required.

Waste Flow Pattern

The waste slurry with desired concentration of organic matter but limited to 50% is prepared and stored in PVC tank, henceforth called feed tank (1). The chemical solutions such as buffer or alkalinity are added through funnel (2) to the feed tank. The contents in the feed tank are continuously mixed with the mixer (3). The slurry is fed by pump (4) through the inlet pipe (5) to the reactor by regulating a valve (6).

The slurry is raised through the constricted portion (7) in to the expanded portion of the column reactor (8). The biodegradable substrate/particulate matter while passing through the sludge bed in the expanded portion gets converted anaerobically to the biogas and the treated slurry with lower substrate concentration is collected from top of the reactor (9) through the outlet pipe (10) and controlled by valve (11) and (12).

The effluent (treated wastewater/slurry) is pumped back with the help of a pump (13) through a pipe with a valve (14) into the constricted portion of the reactor. The bottom opening with a valve (15) is used for excess sludge withdrawal or imparting backwash to the reactor. The reactor can be fed with substrate (slurry/wastewater) or chemicals directly through a funnel with a valve (16). The biogas generated during anaerobic digestion is collected from the top through a pipe (17) with a valve (18) into biogas collection and measurement assembly (19) and biogas sampling port (20). The outlet of the reactor (10) is connected to a settling tank (21) the biogas collection from settling tank (22) is done and sent to common biogas collection and measurement assembly. The effluent is discharged through outlet of settling tank (23) and sludge is withdrawn from the bottom outlet for sludge disposal (24) facility of sampling cum recirculation arrangement from individual constricted portion is provided (25) with valve (26) to control/regulate recirculation rate and valve (27) for using as sampling ports. The complete assembly is supported with the help of stand (28).

The arrangement of the valves and the recirculation line is made in such a way that the flow of the waste slurry can be diverted to the desired part of the reactor. This is very useful in maintaining the necessary environmental conditions of the reactor such as pH, temperature etc. The upflow liquid velocity and flow pattern is helpful in maintaining the partial phase segregation in the reactor.

The units may be interconnected by any sort of external tube connections such that the reactor system has a single inlet and a single outlet. The reactor also has a facility by virtue of its arrangement of valves and recirculation lines, to deploy the required number of portions and to discard the redundant number of column units portions in a particular reactor system. The discarded portions can be used for other purposes such as polishing, disinfection etc. Space available at the top of reactor is useful for gas collection. Gas collection and transporting manifolds can be provided at the top of the reactor system.

Working of the Reactor System

As described above, the reactor typically uses a series of constricted portion (CP) and expanded portion (EP) to enable the waste to flow alternatively through them. As it passes from inlet to outlet, the biomass within the reactor tend to rise and settle while moving vertically at a relatively slow rate. Thus, the wastewater can come in contact with a large amount of active biomass in the system as it passes vertically up through the reactor. The increased mixing of biomass and substrate enhances substrate degradation rate and thereby its bioconversion leading to improved performance efficiency of the reactor. Such a unique arrangement of CP and EP also possesses a better particle trapping mechanism.

The constricted portion (CP) of the column reactor provides accelerated upflow velocity to the waste slurry/wastewater so that the particulate matter in the slurry/wastewater is prevented from settling. In the expanded portion (EP), due to lower liquid velocity continuous settling of the particles takes place. The upward liquid velocity and downward particle settling causes intense mixing of biomass and organic particulate matter.

The vertically compartmentalized structure of the reactor provides partial phase segregation thereby creating adequate environmental conditions to the microbial consortia. These conditions include combination of environmental conditions such as pH, acidity, alkalinity and availability of organics, etc. Besides this, the hydrodynamic conditions such as flow pattern, flow velocity, hydraulic retention time (HRT), solid retention time (SRT) cause the microbial consortia to resort to particular part of the reactor. According to the suitable conditions the bacteria may resort to the different portions of the reactor which eventually favors the growth of the specific bacteria and hence the reaction rate.

The hydrolytic/acidogenic bacteria resort to the bottom part of the reactor whereas methanogenic ones are available at the upper part of the column reactor. Owing to such stratification, the column reactor (CR) behaves as a partially segregated phase reactor. The effluent from preceding portion passes on to the next portion through a CP connection. The treated effluent is finally collected from the top through the reactor outlet.

The alternate arrangement of expanded portions (EP) and constricted portions (CP) in the reactor improves the treatment process in two ways: first, as the sludge particles are captured efficiently and not washed off with the effluent, the mean cell resistance time (MCRT) of the order of 100 days can be achieved at low hydraulic retention time (HRT) of the order of 7 days which in turn increases the treatment efficiency of the reactor. Increase in MCRT at low HRT, reduces the net volume of reactor. The upper tapering part of the EP acts like a gas-solid-liquid separator which helps in arresting the solids escaping with the liquid flow. Hence, escaping of biosolids with the treated effluent is minimum; thereby, enhancing the treatment efficiency at lower HRT. This makes the reactor system compact and techno-economically viable. Due to the excellent inventory control of biomass, the treated effluent quality is consistent and long-term stable performance is achieved.

The reactor system may be consisted of several units of anaerobic column reactor (ACR) connected in series or placed in parallel. The parallel sets of anaerobic column reactor (ACR) may be connected to each other by means of an appropriate connection such as a PVC tube. Such an arrangement is very useful in a way that only required number of CR can be put to operation depending upon the desired degree of treatment and performance efficiency of the reactor. Depending upon the required grade of treatment or required effluent quality, the redundant ACR/portions of ACR can be utilized for polishing the effluent with some form of tertiary treatment such as sand filter, aeration, disinfection etc.

Analysis and Measurements

Samples were taken from the feedstocks (food waste) and digested solids and analyzed for total solids (TS) and volatile solids (VS) contents according to the Standard Methods (APHA, 1998). The seed sludge used for reactor start up was analyzed for mixed liquor volatile suspended solids (MLVSS), mixed liquor suspended solids (MLSS), total solids (TS) and total volatile solids (TVS). The characteristics of seed sludge are shown in Table 1. Daily biogas production from reactor was measured using a wet gas flow meter. The total experimental set up was placed in the controlled temperature room at 35° C. Collected biogas was analyzed periodically for methane and carbon dioxide contents using a gas chromatograph (GC) (Model HP5890A, Hewlett Packard, Avondale, Pa.) equipped with a thermal conductivity detector. The pH of liquid samples from the biogasification effluent and the liquid collection tank were measured prior to loading of reactor using a pH meter (Accumet AR50, Fisher Scientific, Pittsburgh, Pa.).

TABLE 1

Seed Sludge Characteristics

| Parameter | Value |
| --- | --- |
| TS (g/L) | 20.27 |
| VS (g/L) | 11.67 |
| VS (% TS) | 57.6 |
| MLSS (g/L) | 16.73 |
| MLVSS (g/L) | 10.45 |

Reactor Operation

The characteristics of the food waste and its slurry (20% i.e. total slurry concentration of 200 g/L) are given in Table 2 and Table 3 whereas Table 4 illustrates elemental composition of the food waste. Reactor start-up is carried out by using the mixture of cow dung slurry, seed sludge and food waste slurry. The seed sludge is taken from other suspended growth anaerobic reactor. The food waste slurry concentration was maintained at 5%, i.e. 50 g/L (wet weight/volume). The mixture is composed of 50% seed sludge, 30% cow dung slurry and 20% food waste slurry taken by the volume of the reactor. The mixture is retained for 7 days without mixing. On 8th day, the reactor content is recycled continuously with the help of the peristaltic pump connected between the outlet and the inlet of the CR and the feeding of the food slurry is initiated. On 15 day, the biogas production is measured with the help of the wet gas flow meter and the reactor is reckoned as acclimatized. The start-up period of the reactor is 15 days. Subsequently, the other experiments were conducted.

The performance of the CR system is characterized by two parameters: (a) ability to produce methane-rich biogas, which is quantified by daily biogas production volume and methane content of biogas, and (b) effective treatment of the solids waste, which is quantified by TS and VS reductions in the feedstock after digestion. System stability is determined by monitoring pH and daily biogas production of all reactors.

The pH in the system over the start-up period is monitored to determine the stability of the reactor. Over a 200-day period, pH in the reactor increased to and stabilized near 7.2. A low methane content of about 50% is found shortly after loading, whereas a high methane content of about 70% is reached towards the end of the digestion cycle.

The methane content in the biogas produced in the biogasification reactor is consistently higher than the methane content in the biogas produced in the hydrolysis reactors at any point in their batch cycle. This indicates that the methanogenic and hydrolytic bacteria has been separated to some extent into their respective zones in the same reactor.

A linear increase of both biogas and methane production can be seen. The calculated average biogas and methane yields were 600 and 400 mL/gVS, respectively. The TS and VS reductions in the food waste after 15-day digestion were measured to be 84% and 94%, respectively (Table 5).

EXAMPLES

The following examples are given by way of illustration of the working of the invention in actual practice and therefore should not be construed to limit the scope of the present invention:

Example 1

The prototype of present invention was operated in the laboratory for the treatment of food waste slurry with different slurry concentrations. Influent slurry characteristics for 20% slurry concentration were in the following range: chemical oxygen demand (COD): 35500 mg/l and total solids: 20000 mg/l. Physico-chemical characteristics of food waste is given in Table 2 whereas slurry characteristics and elemental analysis of waste slurry at 20% solids concentration are given in Table 3 and Table 4 respectively.

The ratio of total volatile acids (TVA) to the alkalinity was maintained below 0.4 throughout the study. This indicated proper balance between the reactor content, which did not necessitate the addition of alkalinity to the reactor system proving it economical. The volatile solids reduction of 96% was obtained at 5 d HRT. The specific biogas yield at optimum HRT of 5 d was observed to be 0.35 cum.CH4/kgCODr.d with 69% methane content in the biogas. Biogas generation is high due to retention of methanegens for sufficient time.

Adequate availability of methanogenic biomass also enhances the reactors ability to withstand shock loads and to sustain the toxicity. The experimental results are indicated in and Table 5 and Table 6 and the comparative analysis is shown in Table 7.

TABLE 2

Characteristics of Food waste

| Sr. No. | Parameters | Concentration |
|---|---|---|
| 1 | pH | 4.9-5.3 |
| 2 | Moisture Content (%) | 59-63 |
| 3 | TS (g/l) | 200 |
| 4 | TSS (g/l) | 130-165 |
| 5 | TDS (g/l) | 35-70 |
| 6 | VS (g/l) | 170-189 |
| 7 | VS (%) | 94.9 |
| 8 | VSS | 164 |
| 9 | TOC (g/l) | 109 |
| 10 | COD (g/l) | 63 |
| 11 | Sodium (mg/l) | 790 |
| 12 | Potassium (mg/l) | 9300 |
| 13 | Sulphate (mg/l) | 535 |
| 14 | Phosphate (mg/l) | 547 |
| 15 | Nitrate (mg/l) | 180 |
| 16 | Nitrogen (%) | 2 |
| 17 | Protein (%) | 11 |
| 18 | Carbohydrate (%) | 19 |

TABLE 3

Characteristics of FW Slurry (20% d.b)

| Sr. No. | Parameters | Concentration |
|---|---|---|
| 1 | pH | 6.8 |
| 2 | Alkalinity | 600 |
| 3 | CODt (mg/L) | 35500 |
| 4 | CODs (mg/L) | 25600 |
| 5 | Total Solids (mg/L) | 20000 |
| 6 | Suspended Solids (mg/L) | 15400 |

TABLE 4

Elemental Analysis of Food Waste

| Solids (%) | VS (%) | Elemental composition (%) | | | |
|---|---|---|---|---|---|
| | | C | H | N | O |
| 20 | 87 | 50 | 5 | 40 | 5 |

TABLE 5

Performance Evaluation of Anaerobic Column Reactor for Biomethanation of Food Waste

| Parameters | Values |
|---|---|
| Volume | 28 L |
| Loading Rate | 4.3 kg/m$^3$ · d |
| HRT | 5 days |

TABLE 5-continued

Performance Evaluation of Anaerobic Column Reactor for Biomethanation of Food Waste

| Parameters | Values |
|---|---|
| VS removal | 94% |
| CH$_4$ yield | 0.35 m$^3$/kg CODr |

Example 2

The prototype of present invention was operated at various HRTs by varying flow rate of food waste slurry. It was observed that the quality of effluent went on deteriorating as the flow rate of influent wastewater went on increasing. It was observed that after a particular HRT of 5 d, the increase in HRT didn't yield the considerable improvement in effluent quality. Below HRT of 5 d, the pH of treated effluent drastically changed to acidic (pH<5.2). On the other hand, lower HRT than 5 d hampered the effluent quality with COD reduction efficiency reduced to less than 50%. Hence, from the viewpoint of techno-economic effectiveness, HRT of 5 d was established as an appropriate HRT for the reactor while treating municipal wastewater.

Example 3

The influent slurry concentration was maintained at 20%. However, the parameters such as pH, total COD (CODt) and volatile fraction of solids varied in the range of 6.8-7.6, 18000-22000 mg/L, and 65-75% respectively. Performance evaluation study over a period of 200 days demonstrated that although influent feed characteristics and concentrations were changing diurnally, the treated effluent quality at the particular HRT was consistent. The values of pH, biogas generation rate and CODt reduction were obtained to be 7.5, 0.34 m$^3$CH$_4$/kgCODr and 75% respectively during the steady state period of operation. This has confirmed that the reactor is robust enough to handle the variation in wastewater quality and influent feed for yielding consistent effluent quality. This facet of the reactor is quite useful to the industries where variation in the feed quality is frequent. Performance of the anaerobic column reactor with respect to solids reduction and biogas generation is indicated in Table 6.

TABLE 6

Performance the Anaerobic Column Reactor with respect to Solids Reduction and Biogas Generation

| Substrates | Biogas yield (mL/gVS) | Methane yield (mL/gVS) | TS destruction (%) | VS destruction (%) |
|---|---|---|---|---|
| Food waste | 600 | 400 | 84 | 94 |

Example 4

Performance evaluation was carried out for individual expanded portions (EPs) at steady state operational conditions acquired; i.e. HRT of 5 d, influent feed strength of 20000 mg/l COD, and organic loading rate of 4.3 kg COD/m$^3$.d. The study indicated strong hydrolytic and acidogenic activities in the first two EPs, whereas methanogenesis was prevalent in rest of the EPs. The ability of partially segregating acidogenesis and methanogenesis is phenomenal advantage of this reactor configuration.

Reductions in soluble COD of 42%, 45%, 47% and 21% were obtained respectively in the expanded portions $EP_1$, $EP_2$, $EP_3$ and $EP_4$. Similarly, about 75% of the total COD was degraded in the first two EPs only.

It was indicated that first two EPs (EP1 and EP2) were enough for necessary total solids (TS) removal. Most of the total volatile solids (TVS) reduction occurred in EP1 and EP2. The typical arrangement of EP and CP, its size and shape had an effect of velocity reduction, which would arrest more particulate matter by gravity settling. It was revealed that the methanogenic activity was more in prevalent EP3, and EP4.

Example 5

Table 7 illustrates comparative analysis of performance of various treatment systems for biomethanation of food wastes. The analysis clarified that this invention operates at a comparatively lower hydraulic retention time (HRT) than most of the reactors in the market. At the similar organic loading rate (OLR) the volatile solids reduction rate (94%) and the specific methane yield were 94% and 0.96 $m^3$/kgVSr respectively. At the OLR of 4.5 kg/$m^3$·d, the specific methane yield in terms of organics removal was 0.35 $m^3CH_4$/kgCODr.

TABLE 7

Comparative Analysis of Performance of the Invention with Technologies in the Market for Biomethanation of Food Waste

| Parameters | AMBR[1] | AF[2] | Batch Tests[3] | AD[4] | SIR[5] | Invention |
|---|---|---|---|---|---|---|
| Volume (L) | 700 | 15 | — | 0.5 | 5 | 28 |
| Loading Rate | 4.5 kg/$m^3$ d | 0.45 g COD/ld | — | 10.5 vs/L | — | 4.3 kg/$m^3$ · d |
| HRT (d) | 2.1 | — | 6 | 28 | 60 | 5 |
| VS removal % | — | 95.1 | 96 | 80.57% | 49.7% | 94 |
| $CH_4$ yield | 0.136 $m^3$/kg CODr | 0.99 L/g | 0.40 $m^3$/kg VS | 0.44 l/g VS | 0.49 L/g VS | 0.35 $m^3$/kg CODr 0.96 $m^3$/kg VSr |

The experimental study carried out on prototype of invention has led to a conclusion that the invention is appropriate, economical, modular, efficient and effective treatment system that can be used as a decentralized on-site treatment package for but not limited to hotels, bakeries, individual dwellings colonies, agro-industries, food processing units and other industries or processes generating biodegradable wastes.

THE MAIN ADVANTAGES OF THE PRESENT INVENTION

The treatment efficiency is higher than other existing reactors for low, medium and high strength feed due to its capability to maintain high mean cell residence time (high MCRT) by retaining the biomass for longer periods and inducing high mass transfer rate.

Due to compartmentalized geometry, partial segregation of different phases of anaerobic biodegradation (such as hydrolytic, acidogenic and methanogenic processes) has become possible within the same reactor without demerits and liabilities of the separate phase reactors.

Efficient treatment of colloidal and particulate wastewaters is also possible due to compartmentalization which enhances the hydrolysis in the lower portions at low pH and methnogenesis in upper portions remain undisturbed.

Biogas collection is made easy and efficient. The partial segregation of acidogenic & methanogenic process also gives enhanced specific biogas yield ($m^3$ $CH_4$/kg-$COD_r$).

The reactor by virtue of specific arrangement of constricted portions (CP) and expanded portions (EP) and distinct flow pattern do not require flocculated sludge/granules formation. This reduces the start-up period because granular sludge is difficult not only to develop but also to be retained for longer duration as essential in UASB system.

Owing to the compartmentalized reactor configuration and effective biomass inventory, the reactor withstands effectively the fluctuations in hydraulic and organic overloads and it can recover from shock loads within a reasonable period of time yet yielding consistent quality of effluent.

The reactor system has, except feed pump and recirculating pump, no moving parts and/or mechanical mixing devices it is simple and easy for construction/fabrication, installation and operation; it consumes less power for pumping & hence low cost of operation and maintenance. In addition, it does not require any special gas-solid-liquid separator or sludge separation system.

Innovative constructional features of the proposed reactor facilitate use of only required number of portions while redundant portion can be used for other purposes such as storage of treated effluent and/or its tertiary treatment before final discharge.

Due to modular design, the reactor can be retrofitted in the existing treatment systems for the purposes such as efficient rigorous mixing, anaerobic digestion, biogas generation and collection etc.

The mechanism for biogas collection/storage mechanism and the effluent collection is effective to eliminate biogas escape with the effluent.

Other advantages include: no media requirement, no need of mechanical mixing, availability of maximum effective volume for biomass development and its retention for sufficient period; minimum floor area requirement due to its unique construction features; ease of biogas collection and minimum pumping energy requirement.

We claim:

1. An anaerobic column reactor for conversion of biodegradable organic matter present in wastewaters and solid wastes into biogas and compost; said reactor consisting essentially of a column of at least four expanded portions (EP), connected to each other by constricted portions (CP), waste feeding and chemicals feeding facility, biogas collection sampling and measurement assembly, slurry/digestate recirculation assembly, with backwash facility;

wherein, the waste feeding and chemicals feeding either through inlet pipe (5) with a pump (4) and regulating valve (6) or directly through a funnel with a valve (16); the biogas collection sampling and measurement assembly connected through a pipe (17) with a valve (18); the slurry/digestate recirculation through a pipe with a pump (13) and a valve (14) into the constricted portion; and the bottom opening of the reactor with a valve (15) to impart backwash facility.

2. An anaerobic column reactor (100) for conversion of biodegradable organic matter present in wastewaters and solid wastes into biogas and compost, said reactor having a feed tank (1) equipped with waste feeding funnel (2), mixing arrangement (3), feed pump (4), inlet pipe (5), regulating valves (6), said reactor (100) having a constricted portion (7) and expanded portion (8), recirculation pipe (9), outlet (10), valves (11) and (12), slurry recirculation facility (13) (14) (15), chemicals feeding facility (16), biogas collection facility (17) (18), sampling and a measurement assembly (19) (20), outlet pipe (10) of reactor connected to a settling tank (21), a biogas collection assembly (22) connected with outlet (23), sludge disposal outlet (24), and slurry/digestate recirculation arrangement (25) connected with valves (26) (27) and a stand (28) to support the column reactor; wherein the chemicals feeding facility directly through a funnel with a valve (16); the slurry recirculation facility through a pipe with a pump (13) and a valve (14) into the constricted portion and a valve (15) to impart backwash facility.

3. The anaerobic column reactor according to claim 2, wherein said reactor (100) consisting a column of at least four alternate expanded portions (8) connected to each other by constricted portions (7).

4. The anaerobic column reactor according to claim 2, wherein alternate expanded portions (8) and constricted portions (7) are connected in series that the reactor has a single outlet (23) and single biogas collection point.

5. The anaerobic column reactor according to claim 2, wherein said reactor (100) is operated in a batch mode, semi-continuous or continuous mode with automated or manual operation possible.

6. The anaerobic column reactor according to claim 2, wherein alternate expanded portions (8) are interconnected through a recirculation pipe (9) is facilitate recirculation of digested from a particular expanded portion (8) with the help of the inlet (5) connected with controlling valves (6).

7. The anaerobic column reactor according to claim 2, wherein biogas collection assembly (17, 18, 22) sampling and measurement assembly (19, 20) is provided to facilitate biogas collection from the reactor (100) and settling tank (21).

8. The anaerobic column reactor according to claim 2, wherein the funnel (2, 16) with valve (6) is being used for waste feeding and chemicals feeding facility respectively.

9. The anaerobic column reactor according to claim 2, wherein settling tank (21) is provided with effluent outlet (23) for removal of clarified effluent and sludge disposal outlet (24) at the bottom of the settling tank (21) for the discharge of the settled sludge.

10. The anaerobic column reactor according to claim 1, wherein mixed culture of consortia anaerobic microorganisms is being used to digest organic biodegradable waste to biogas and compost.

11. The anaerobic column reactor according to claim 1, wherein the biodegradable wastes is selected from biodegradable solid wastes, waste water and aqueous slurry of biomass, fruits, vegetables, agro-processing waste, animal compost, poultry wastes, aquatic plants, fraction of municipal solid wastes, energy crops and combinations thereof.

12. The anaerobic column reactor according to claim 2, wherein mixed culture of consortia anaerobic microorganisms is being used to digest organic biodegradable waste to biogas and compost.

13. The anaerobic column reactor according to claim 2, wherein the biodegradable wastes is selected from biodegradable solid wastes, waste water and aqueous slurry of biomass, fruits, vegetables, agro-processing waste, animal compost, poultry wastes, aquatic plants, fraction of municipal solid wastes, energy crops and combinations thereof.

14. A process for the conversion of biodegradable wastes into biogas and compost by using the reactor according to claim 2, wherein the process steps comprises:
   a. pumping the wastes and passing from inlet (5) at the bottom to outlet (23) at the top through constricted portion (7) and expanded portion (8);
   b. degrading wastes by mixing wastes with the culture of consortia anaerobic microorganism the reactor to obtain slurry;
   c. recirculating the slurry obtained in step (b) in the reactor through recirculation pump (9) to produce biogas;
   d. collecting the biogas generated in step (c) from settling tank (21) and biogas collection sampling assembly (17, 18) and measurement assembly (19, 20);
   collecting sludge from the setting tank (21) through sludge disposal outlet obtained in step (c) and sent for its disposal.

* * * * *